United States Patent
Stalling et al.

(10) Patent No.: US 12,157,326 B2
(45) Date of Patent: Dec. 3, 2024

(54) HEAT-SENSITIVE RECORDING MATERIAL

(71) Applicant: KOEHLER INNOVATION & TECHNOLOGY GMBH, Oberkirch (DE)

(72) Inventors: Timo Stalling, Appenweier (DE); Michael Horn, Offenburg (DE)

(73) Assignee: Koehler Innovation & Technology GmbH, Oberkirch (DE)

( * ) Notice: Subject to any disclaimer, the term of this patent is extended or adjusted under 35 U.S.C. 154(b) by 116 days.

(21) Appl. No.: 17/923,841

(22) PCT Filed: Mar. 29, 2021

(86) PCT No.: PCT/EP2021/058119
§ 371 (c)(1),
(2) Date: Nov. 7, 2022

(87) PCT Pub. No.: WO2021/223939
PCT Pub. Date: Nov. 11, 2021

(65) Prior Publication Data
US 2023/0202220 A1    Jun. 29, 2023

(30) Foreign Application Priority Data
May 7, 2020   (DE) ..................... 10 2020 112 411.2

(51) Int. Cl.
*B41M 5/333* (2006.01)
*C07C 309/76* (2006.01)
*B41M 5/327* (2006.01)

(52) U.S. Cl.
CPC ......... *B41M 5/3333* (2013.01); *C07C 309/76* (2013.01); *B41M 5/3275* (2013.01); *B41M 2205/04* (2013.01)

(58) Field of Classification Search
CPC .............. B41M 5/3275; B41M 5/3333; B41M 5/3375; B41M 2205/04; C07C 309/76
See application file for complete search history.

(56) References Cited

U.S. PATENT DOCUMENTS 4,504,490 A * 3/1985 Rosner .................. C07C 323/66
514/483

FOREIGN PATENT DOCUMENTS

| | | |
|---|---|---|
| CN | 106536209 A | 3/2017 |
| EP | 0526072 A1 | 2/1993 |
| EP | 0633145 A1 | 1/1995 |
| EP | 0620122 B1 | 3/1996 |
| EP | 2923851 A1 | 9/2015 |
| EP | 3395583 A1 | 10/2018 |
| JP | 60-162689 A | 8/1985 |
| JP | 06-227142 A | 8/1994 |
| JP | 07-068945 A | 3/1995 |
| JP | 8-002109 A | 1/1996 |
| JP | H11268422 A | 10/1999 |
| WO | 2017111032 A1 | 6/2017 |
| WO | 2018/145874 A1 | 8/2018 |
| WO | 2018215287 A1 | 11/2018 |
| WO | WO-2019044462 A1 * | 3/2019 ............ B41M 5/323 |
| WO | WO-2021171983 A1 * | 9/2021 ............ B41M 5/323 |

OTHER PUBLICATIONS

Notice of Reasons for Refusal for Japanese Patent Application No. 2022-567394, dated Dec. 8, 2023, 21 pages.
Anonymous: "Registry—RN 406713-68-6, entered STN Apr. 23, 2022—Benzenesulfonic acid 4- chloro- 3 - [[[(4-fluorophenyl)amino]carbonyl]amino] - 4- [[[(4-fluorophenyl)amino]carbonyl]amino]phenylester", Apr. 23, 2002.
Anonymous: "Reaxys - 4-({[4-fluorophenyl)amino]carbonyl}amino)phenyl 4-chloro-3-({[4-fluoro phenyl)amino]carbonyl}amino)benzenesulfonate", Reaxys Database, Jun. 10, 2021.
International Search Report for PCT/EP2021/058119, mailed Jun. 24, 2021, 6 pages.
Office Action for Indian Patent Application No. 202217067787, dated Apr. 30, 2024, 6 pages.
Office Action for Chinese Patent Application No. 202180033419.5, dated May 31, 2024, 13 pages.

* cited by examiner

*Primary Examiner* — Gerard Higgins
(74) *Attorney, Agent, or Firm* — Lippes Mathias LLP

(57) ABSTRACT

Described are colour developers of formula (I)

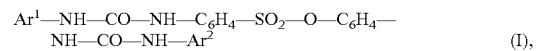

$$Ar^1{-}NH{-}CO{-}NH{-}C_6H_4{-}SO_2{-}O{-}C_6H_4{-}NH{-}CO{-}NH{-}Ar^2 \quad (I),$$

a heat-sensitive recording material comprising a carrier substrate and also a heat-sensitive, colour-forming layer containing at least one colour former and at least one phenol-free colour developer, wherein the at least one colour developer is the compound of formula (I), and a method for producing this heat-sensitive recording material.

20 Claims, No Drawings

HEAT-SENSITIVE RECORDING MATERIAL

The invention relates to a colour developer, to a heat-sensitive recording material comprising a carrier substrate and also a heat-sensitive, colour-forming layer containing at least one colour former and at least one phenol-free colour developer, and also to a method for producing this heat-sensitive recording material.

Heat-sensitive recording materials (thermal papers) for direct thermal printing applications which have a heat-sensitive colour-forming layer (thermal reaction layer) applied to a carrier substrate have been known for a long time.

The heat-sensitive colour-forming layer usually contains a colour former and a colour developer, which react with each other under the influence of heat and thus lead to colour development. Inexpensive (bis)phenolic colour developers, such as bisphenol A and bisphenol S, are widespread and can be used to obtain heat-sensitive recording materials with an acceptable performance profile for numerous applications. Also known are heat-sensitive recording materials that contain a non-phenolic colour developer in the heat-sensitive colour-forming layer. These have been developed to improve the resistance of the typeface, especially if the printed heat-sensitive recording material is to be stored for longer periods of time at higher temperatures and/or humidity. Especially against the background of the public discussions regarding the toxic potential of (bis)phenolic chemicals, interest in non-phenolic colour developers has risen sharply. The aim here was to avoid the disadvantages of (bis)phenolic colour developers, but to at least maintain, and preferably improve, the technical performance properties that can be achieved with phenolic colour developers.

The prior art on non-phenolic colour developers reveals common structural characteristics despite the great chemical diversity of these substances.

For example, a 1,3-disubstituted (thio)ureido substructure (Y—NH—C(X)—NH—Z with X=S or O) is a common feature of numerous non-phenolic colour developers.

The functional properties relevant for suitability as a colour developer can be modulated by appropriate selection of the Y and Z groups.

Colour developers with sulfonylurea structures (—$SO_2$—NH—CO—NH—) are widely used because they are relatively easy to produce and the heat-sensitive recording materials they produce have good application properties.

EP 0 526 072 A1 and EP 0 620 122 B1 disclose colour developers from the class of aromatic sulfonyl(thio)ureas. With these, heat-sensitive recording materials can be obtained that are characterised by a relatively high image resistance. Furthermore, the heat-sensitive recording materials based on these colour developers have a useful thermal sensitivity with good surface whiteness, so that, if the formulation of the heat-sensitive colour-forming layer is appropriately designed, it is comparatively easy to produce high print densities using commercially available thermal printers.

WO 0 035 679 A1 discloses aromatic and heteroaromatic sulfonyl(thio)urea compounds (X=S or O) and/or sulfonyl guanidines (X=NH) of the formula Ar'—$SO_2$—NH—C(X)—NH—Ar, wherein Ar is linked to other aromatic groups by a divalent linker group. A non-phenolic colour developer from this class, 4-methyl-N-(((3-(((4-methylphenyl)sulfonyl)oxy)phenyl)amino)carbonyl)benzenesulfonamide (trade name Pergafast 201®, BASF), which is widely used in practice, is characterised by the balance of the application properties of the heat-sensitive recording materials produced with this colour developer. Especially, these materials have good dynamic responsiveness and, compared to recording materials obtained with (bis)phenolic colour developers, higher resistance of the print when stored under harsh environmental conditions or with respect to hydrophobic substances.

Sulfonylureas tend towards hydrolytic decomposition reactions in the presence of water/moisture and in heat (M. Eckhardt, T. J. Simat, Chemosphere, 186, 1016 (2017)). As a result, heat-sensitive recording materials may experience partial decomposition of the colour developer when stored in the unprinted state under conditions of elevated humidity and/or temperature.

Since the writing performance (dynamic responsiveness) of heat-sensitive recording materials is dependent on the amount of colour developer present in the heat-sensitive layer, a heat-sensitive recording material stored for longer periods of time loses part of the colour developer and thus loses some of its writing performance.

The above-mentioned possibility of modulating the properties of the 1,3-disubstituted (thio)ureido sub-structure can also be achieved by including structural units that are favourably conjugated to the ureido unit.

Such an approach was adopted for example in EP 2 923 851 A1. For example, EP 2 923 851 A1 discloses colour developers of the general formula $R^1$—NH—CO—NH—Ar—NH—$SO_2$—$R^2$, wherein $R^1$, $R^2$ and Ar may be (un)substituted aryl groups. A widely used non-phenolic colour developer from this class is N-(2-(3-phenylureido)phenyl)benzenesulfonamide (trade name NKK 1304®, Nippon Soda Co. Ltd.). Although a good dynamic sensitivity can be ensured with the heat-sensitive recording materials based on these colour developers, the stability of the colour complex—especially in relation to plasticisers or adhesives—requires improvement.

A comparable concept was also provided in WO 2017 111032 A1, which discloses colour developers of general formula Ph-NH—CO—NH—$C_6H_4$—O—$SO_2$—Ar, wherein Ar may be a (un)substituted phenyl group.

Already from an early stage, it was attempted to improve the performance of non-phenolic colour developers by using colour developer structures that contain more than just one of the structural units relevant for the colour formation process.

JP H 06 227 142 A discloses colour developers having two, three or more (thio)urea units (bis-, tris-, polykis-ureas) in the compound $Ar^1$—NH—C(X)—NH)$_n$-A, which are bound to a usually aromatic unit A (X=S or O). The colour developers described in EP 633 145 A1, JP H 0 821 109 A, JP H 08 244 355 A and JP H 11 268 422 A are of a similar structure.

Although bis- or polykis-urea derivatives have good hydrogen bridge acceptor and donor properties and are therefore suitable for stabilising the colour complex, the hydrogen bridge networks that form between the individual urea units result in a relatively high melting point and a low solubility of these substances in typical thermal solvents from the heat-sensitive layer, and therefore the thermal responsiveness (so-called dynamic sensitivity) of the heat-sensitive recording materials produced using these colour developers leaves a lot to be desired.

The aim of the present invention is therefore to overcome the disadvantages of the prior art described above. Especially, the aim of the present invention lies in providing a colour developer and a heat-sensitive recording material containing same, which recording material has a balanced application property profile and achieves a print density suitable for practical use, comparable to that of heat-sensitive recording materials based on known non-phenolic colour developer agents, but at the same time ensures a high resistance of the printed image, especially when the heat-sensitive layer is contacted with hydrophobic substances, such as plasticisers from film materials, oils, fats, and the like, preferably without having to rely on special formulation components in the heat-sensitive function layer, such as anti-degradation agents or special melting aids with limited availability and/or high price. A further aim of the present invention is to provide a colour developer or a heat-sensitive recording material which is able to ensure the functional properties required for application (especially the thermal responsiveness), even when the unprinted heat-sensitive recording material is stored for longer periods of time and/or under extreme climatic conditions (high humidity and/or temperature).

In accordance with the invention these aims are addressed by the use of a compound according to claim 1 in a heat-sensitive recording material according to claim 10.

It has surprisingly been found that it is possible, using colour developers from class (I) according to the invention, to obtain heat-sensitive recording materials that are distinguished by excellent resistance of the typeface, especially even if the printed image is exposed to hydrophobic substances such as plasticisers. The recording materials produced with the colour developers according to the invention also have excellent long-term storage stability. The typeface achieved in thermal printers thus hardly suffers, not even after storage in the unprinted (white) state over several weeks with high ambient humidity and/or at high temperatures.

The compound according to claim 1 has the formula (I),

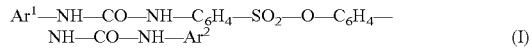

$$Ar^1\text{—}NH\text{—}CO\text{—}NH\text{—}C_6H_4\text{—}SO_2\text{—}O\text{—}C_6H_4\text{—}NH\text{—}CO\text{—}NH\text{—}Ar^2 \quad (I)$$

wherein $Ar^1$ and $Ar^2$ independently of one another are an unsubstituted or substituted phenyl group, naphthyl group and/or heteroaryl group.

$Ar^1$ is preferably a phenyl group.

$Ar^2$ is preferably a phenyl group.

Preferably, $Ar^1$ is substituted with at least one $C_1$-$C_5$ alkyl group, an alkenyl group, an alkynyl group, a benzyl group, a formyl group, a halogen group, an $NO_2$ group, a CN group, an R—CO— group, an RO group, an $RO_2C$ group, an R—OCO group, an R—$SO_2O$ group, an R—O—$SO_2$ group, an R—$SO_2$—NH group, an R—NH—$SO_2$ group, an R—NH—CO group or an R—CO—NH group, wherein R is a $C_1$-$C_5$ alkyl group, an alkenyl group, an alkynyl group, a phenyl group, a tolyl group, or a benzyl group.

$Ar^1$ is especially preferably substituted with at least one $C_1$-$C_5$ alkyl group, a halogen group, an $NO_2$ group, a CN group, an R—CO group, an RO group or an $RO_2C$ group, wherein R is a $C_1$-$C_5$ alkyl group.

$Ar^1$ is preferably substituted once.

$Ar^1$ is preferably a phenyl group substituted once.

Preferably, $Ar^2$ is substituted with at least one $C_1$-$C_5$ alkyl group, an alkenyl group, an alkynyl group, a benzyl group, a formyl group, a halogen group, an $NO_2$ group, a CN group, an R—CO— group, an RO group, an $RO_2C$ group, an R—OCO group, an R—$SO_2O$ group, an R—O—$SO_2$ group, an R—$SO_2$—NH group, an R—NH—$SO_2$ group, an R—NH—CO group or an R—CO—NH group, wherein R is a $C_1$-$C_5$ alkyl group, an alkenyl group, an alkynyl group, a phenyl group, a tolyl group, or a benzyl group.

$Ar^2$ is especially preferably substituted with at least one $C_1$-$C_5$ alkyl group, a halogen group, an $NO_2$ group, a CN group, an R—CO group, an RO group or an $RO_2C$ group, wherein R is a $C_1$-$C_5$ alkyl group.

$Ar^2$ is preferably substituted once.

$Ar^2$ is preferably a phenyl group substituted once.

$Ar^1$ and/or $Ar^2$ are/is substituted with at least one $C_1$-$C_5$ alkyl group, preferably in such a way that the $C_1$-$C_5$ alkyl group is a methyl group or butyl group, especially preferably a methyl group.

$Ar^1$ and/or $Ar^2$ are/is substituted with at least one halogen group, preferably in such a way that the halogen group is a chloride group and/or a fluoride group.

$Ar^1$ and/or $Ar^2$ are/is substituted with at least one RO group, preferably in such a way that the RO group is a $CH_3O$ group.

$Ar^1$ and/or $Ar^2$ are/is substituted with at least one R—CO group, preferably in such a way that the R—CO group is a $CH_3$—CO group.

In an especially preferred embodiment, both $Ar^1$ and $Ar^2$ are a phenyl group. Such compounds are relatively easy and inexpensive to produce and deliver good results in respect of the properties described below.

In an especially preferred embodiment, the $Ar^1$—NH—CO—NH group and the $Ar^2$—NH—CO—NH group are arranged respectively in the 2 and 3', in the 2 and 4', in the 3 and 2', in the 3 and 3', in the 3 and 4', in the 4 and 2', in the 4 and 3' or in the 4 and 4' position relative to the —$C_6H_4$—$SO_2$—O—$C_6H_4$ group.

The arrangement in the 3 and 2' or 4 and 3' position is especially preferred, since such compounds are relatively easy to produce and show good properties.

Especially preferred compounds of formula (I) are shown in Table 1 below:

TABLE 1

Preferred compounds of formula (1) with the stated meanings for the arrangement of the Ar—NH—CO—NH and $Ar^2$—NH—CO—NH groups as well as the stated meaning of $Ar^1$ and $Ar^2$ (R as mentioned above).

| Arrangement of $Ar^1$—NH—CO—NH— and $Ar^2$—NH—CO—NH— on the —$C_6H_4$—$SO_2$—O—$C_6H_4$ group | $Ar^1$ | $Ar^2$ |
|---|---|---|
| 2,3' | phenyl | phenyl |
| 2,4' | phenyl | phenyl |
| 3,2' | phenyl | phenyl |
| 3,3' | phenyl | phenyl |
| 3,4' | phenyl | phenyl |
| 4,2' | phenyl | phenyl |
| 4,3' | phenyl | phenyl |
| 4,4' | phenyl | phenyl |
| 4,3' | $C_1$—$C_5$-alkyl-substituted phenyl | $C_1$—$C_5$-alkyl-substituted phenyl |
| 4,3' | 1-naphthyl | 1-naphthyl |
| 4,3' | RO-substituted phenyl | RO-substituted phenyl |
| 4,3' | halogen-substituted phenyl | halogen-substituted phenyl |
| 4,3' | RO-substituted phenyl | RO-substituted phenyl |
| 4,3' | $RO_2C$-substituted phenyl | $RO_2C$-substituted phenyl |
| 4,3' | CN-substituted phenyl | CN-substituted phenyl |
| 4,3' | nitro-substituted phenyl | nitro-substituted phenyl |
| 4,3' | RO-substituted phenyl | nitro-substituted phenyl |

TABLE 1-continued

Preferred compounds of formula (1) with the stated meanings for the arrangement of the Ar—NH—CO—NH and Ar$^2$—NH—CO—NH groups as well as the stated meaning of Ar$^1$ and Ar$^2$ (R as mentioned above).

| Arrangement of Ar$^1$—NH—CO—NH— and Ar$^2$—NH—CO—NH— on the —C$_6$H$_4$—SO$_2$—O—C$_6$H$_4$ group | Ar$^1$ | Ar$^2$ |
|---|---|---|
| 4,3' | nitro-substituted phenyl | RO-substituted phenyl |

The compound of formula (I) according to the invention can be produced by methods known per se.

Reaction schemes 1 to 3 illustrate a possible synthesis pathway for the compound of formula (I) according to the invention using the example of the compounds according to Table 1.

Reaction scheme 1

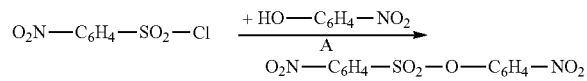

Reaction scheme 2

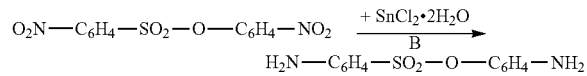

Reaction scheme 3

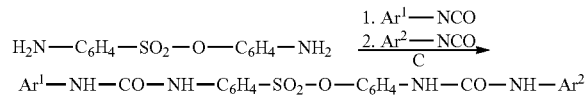

(Ar$^1$, Ar$^2$: see Table 1)

The preferred embodiments listed in conjunction with the compound of formula (I) also apply to the method for producing said compound.

As mentioned, the present invention also relates to a heat-sensitive recording material, comprising a carrier substrate and also a heat-sensitive, colour-forming layer containing at least one colour former and at least one phenol-free colour developer, the at least one phenol-free colour developer being the compound of the above-described formula (I).

The compound of formula (I) is preferably present in an amount of from about 3 to about 35% by weight, especially preferably in an amount of from about 10 to about 25% by weight, in relation to the total solids content of the heat-sensitive layer.

The selection of the carrier substrate is not critical. However, it is preferable to use paper, synthetic paper and/or a plastics film as the carrier substrate.

If necessary, there is at least one further intermediate layer between the carrier substrate and the heat-sensitive layer, with this intermediate layer having the task of improving the surface smoothness of the carrier for the heat-sensitive layer and providing a thermal barrier between the carrier paper and the heat-sensitive layer. Preferably, organic hollow sphere pigments and/or calcined kaolins are used in this intermediate layer.

At least one protective layer and/or at least one layer promoting printability may also be present in the heat-sensitive recording material according to the invention, and these layers may be applied to the front or rear side of the substrate.

With regard to the choice of colour former, the present invention is also not subject to any major restrictions. However, the colour former is preferably a dye of the triphenylmethane type, the fluoran type, the azaphthalide type and/or the fluorene type. A fluoran-type dye is a very especially preferred colour former, since its availability and balanced application properties make it possible to provide a recording material having an attractive price-performance ratio.

Especially preferred fluoran-type dyes are as follows:
3-diethylamino-6-methyl-7-anilinofluoran,
3-(N-ethyl-N-p-toludineamino)-6-methyl-7-anilinofluoran,
3-(N-ethyl-N-isoamylamino)-6-methyl-7-anilinofluoran,
3-diethylamino-6-methyl-7-(o,p-dimethylanilino)fluoran,
3-pyrrolidino-6-methyl-7-anilinofluoran,
3-(cyclohexyl-N-methylamino)-6-methyl-7-anilinofluoran,
3-diethylannino-7-(m-trifluoromethylanilino)fluoran,
3-N-n-dibutylannino-6-methyl-7-anilinofluoran,
3-diethylamino-6-methyl-7-(m-methylanilino)fluoran,
3-N-n-dibutylamino-7-(o-chloroanilino)fluoran,
3-(N-ethyl-N-tetrahydrofurfurylamino)-6-methyl-7-anilinofluoran,
3-(N-methyl-N-propylamino)-6-methyl-7-anilinofluoran,
3-(N-ethyl-N-ethoxypropylamino)-6-methyl-7-anilinofluoran,
3-(N-ethyl-N-isobutylamino)-6-methyl-7-anilinofluoran and/or
3-dipentylamino-6-methyl-7-anilinofluoran.

The colour formers can be used as single substances, but also as arbitrary mixtures of two or more colour formers, provided that the desirable application properties of the recording materials do not suffer as a result.

The colour former is preferably present in an amount of from about 5 to about 30% by weight, especially preferably in an amount of from about 8 to about 20% by weight, in relation to the total solids content of the heat-sensitive layer.

To control specific application properties, it may be advantageous if at least two of the compounds falling under the general formula (I) are present as colour developers in the heat-sensitive layer.

Likewise, one or more other (bis)phenolic or non-phenolic colour developer(s) may be present in the heat sensitive colour-forming layer in addition to the compound(s) of formula (I).

In addition to the at least one colour former and the at least one colour developer, the heat-sensitive colour-forming layer may contain one or more sensitising agents, also known as thermal solvents, which has the advantage that it is easier to control the thermal pressure sensitivity.

In general, crystalline substances with a melting point between about 90° C. and about 150° C. are advantageously used as sensitising agents, and, in the molten state, dissolve the colour-forming components (colour former and colour developer) without disturbing the formation of the colour complex.

Preferably, the sensitising agent is a fatty acid amide, such as stearamide, behenamide or palmitamide, an ethylene-bis-fatty acid amide, such as N,N'-ethylene-bis-stearic acid amide or N,N-ethylene-bis-oleic acid amide, a fatty acid alkanolamide, such as N-(hydroxymethyl)stearamide, N-hydroxymethylpalmitamide or hydroxyethylstearamide, a wax, such as polyethylene wax or montan wax, a carboxylic acid ester, such as dimethyl terephthalate, dibenzyl terephthalate, benzyl-4-benzyloxybenzoate, di-(4-methylbenzyl)oxalate, di-(4-chlorobenzyl)oxalate or di-(4-benzyl)oxalate, ketones such as 4-acetylbiphenyl, an aromatic ether such as 1,2-diphenoxy-ethane, 1,2-di(3-methylphenoxy)ethane, 2-benzyloxynaphthalene, 1,2-bis(phenoxymethyl)benzene or 1,4-diethoxynaphthalene, an aromatic sulfone, such as diphenylsulfone, and/or an aromatic sulfonamide, such as 4-toluenesulfonamide, benzenesulfonanilide or N-benzyl-4-toluenesulfonamide, or aromatic hydrocarbons, such as 4-benzylbiphenyl.

The sensitising agent is preferably present in an amount of from about 10 to about 40% by weight, especially preferably in an amount of from about 15 to about 25% by weight, in relation to the total solids content of the heat-sensitive layer.

In addition to the colour former, the phenol-free colour developer and the sensitising agent, in a further preferred embodiment at least one stabiliser (anti-degradation agent) is optionally present in the heat-sensitive colour-forming layer.

The stabiliser is preferably constituted by sterically hindered phenols, especially preferably 1,1,3-tris-(2-methyl-4-hydroxy-5-cyclohexyl-phenyl)-butane, 1,1,3-tris-(2-methyl-4-hydroxy-5-tert-butylphenyl)-butane, 1,1-bis-(2-methyl-4-hydroxy-5-tert-butyl-phenyl)-butane.

Also urea-urethane compounds of general formula (II) (commercial product UU) or ethers derived from 4,4'-dihydroxydiphenylsulfone, such as 4-benzyloxy-4'-(2-methylglycidyloxy)-diphenylsulfone (trade name NTZ-95®, Nippon Soda Co. Ltd.), or oligomeric ethers of general formula (III) (trade name D90®, Nippon Soda Co. Ltd.) can be used as stabilisers in the recording material according to the invention.

modified polyvinyl alcohols, or styrene-maleic anhydride copolymers, styrene-butadiene copolymers, acrylamide-(meth)acrylate copolymers, acrylamide-acrylate-methacrylate terpolymers, polyacrylates, poly(meth)acrylic acid esters, acrylate-butadiene copolymers, polyvinyl acetates and/or acrylonitrile-butadiene copolymers.

In a further preferred embodiment, at least one release agent (anti-stick agent) or lubricant is present in the heat-sensitive colour-forming layer. These agents are preferably fatty acid metal salts, such as zinc stearate or calcium stearate, or behenate salts, synthetic waxes, for example in the form of fatty acid amides, such as stearic acid amide and behenic acid amide, fatty acid alkanol amides, such as stearic acid methylolamide, paraffin waxes of different melting points, ester waxes of different molecular weights, ethylene waxes, propylene waxes of different hardnesses and/or natural waxes, such as carnauba wax or montan wax.

The release agent is preferably present in an amount of from about 1 to about 10% by weight, especially preferably in an amount of from about 3 to about 6% by weight, in relation to the total solids content of the heat-sensitive layer.

In a further preferred embodiment, the heat-sensitive colour-forming layer contains pigments. One of the advantages of using these pigments is that they can fix on their surface the molten chemicals produced in the thermal printing process. Pigments can also be used to control the surface whiteness and opacity of the heat-sensitive colour-forming layer and its printability with conventional inks. Lastly, pigments have an "extender function", for example for the relatively expensive colouring functional chemicals.

Especially suitable pigments are inorganic pigments, both synthetic and natural, preferably clays, precipitated or natural calcium carbonates, aluminium oxides, aluminium hydroxides, silicas, precipitated and pyrogenic silicas (for example Aerodisp® types), diatomaceous earths, magnesium carbonates, talc, kaolin, but also organic pigments, such as hollow pigments with a styrene/acrylate copolymer wall or urea/formaldehyde condensation polymers. These can be used alone or in any mixture.

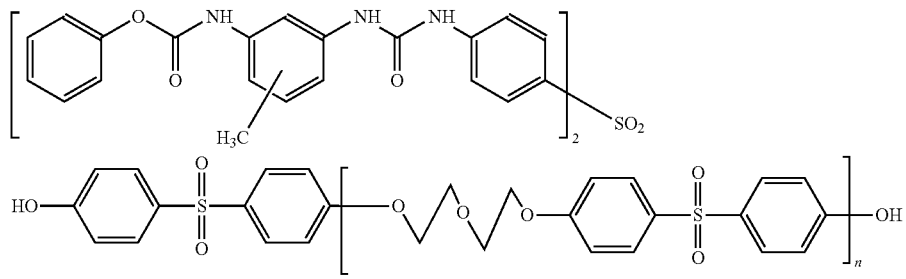

The urea-urethane compounds of general formula (II) are especially preferred.

The stabiliser is preferably present in an amount of about 0.2 to 0.5 parts by weight, in relation to 1 part by weight of the at least one phenol-free colour developer of the compound of formula (I).

In a further preferred embodiment, the heat-sensitive colour-forming layer contains at least one binder. These are preferably water-soluble starches, starch derivatives, starch-based biolatices of the EcoSphere® type, methyl cellulose, hydroxyethyl cellulose, carboxymethyl celluloses, partially or completely saponified polyvinyl alcohols, chemically The pigments are preferably present in an amount of from about 20 to about 50% by weight, especially preferably in an amount of from about 30 to about 40% by weight, in relation to the total solids content of the heat-sensitive layer.

To control the surface whiteness of the heat-sensitive recording material according to the invention, optical brighteners can be incorporated into the heat-sensitive colour-forming layer. These are preferably stilbenes.

In order to improve certain coating properties, it is preferable in individual cases to add further components, especially rheological auxiliaries such as thickeners and/or surfactants, to the mandatory components of the heat-sensitive recording material according to the invention.

The applied weight per unit area of the (dry) heat-sensitive layer is preferably about 1 to about 10 g/m², preferably about 3 to about 6 g/m².

In an especially preferred embodiment, the heat-sensitive recording material is one according to claim 10, in which a dye of the fluoran type is used as colour former and a sensitising agent, selected from the group consisting of fatty acid amides, aromatic sulfones and/or aromatic ethers, is additionally present. In this preferred embodiment it is also advantageous that about 1.5 to about 4 parts by weight of the phenol-free colour developer according to claim 1 are present in relation to 1 part by weight colour former.

The preferred embodiments listed in conjunction with the compound of formula (I) also apply to the heat-sensitive recording material according to the invention.

The heat-sensitive recording material according to the invention can be obtained using known production methods.

However, it is preferable to obtain the recording material according to the invention by a method in which an aqueous suspension containing the starting materials of the heat-sensitive colour-forming layer is applied to a carrier substrate and dried, the aqueous application suspension having a solids content of from about 20 to about 75% by weight, preferably of from about 30 to about 50% by weight, and is applied and dried by the curtain coating process at an operating speed of the coating plant of at least about 400 m/min.

This method is especially advantageous from an economic point of view.

If the solids content falls below the value of about 20% by weight, the economic efficiency is reduced because a large amount of water must be removed from the coating by gentle drying in a short time, which has a negative effect on the coating speed. If, on the other hand, the value of 75% by weight is exceeded, then this only leads to an increased technical effort to ensure the stability of the coating colour curtain during the coating process.

In the curtain coating process, a free-falling curtain of a coating dispersion is formed. By free fall, the coating dispersion, which is in the form of a thin film (curtain), is "poured" onto a substrate to apply the coating dispersion to the substrate. Document DE 10 196 052 T1 discloses the use of the curtain coating process in the production of information recording materials, also including, amongst other things, heat-sensitive recording materials, wherein multi-layer recording layers are realised by applying the curtain, which consists of several coating dispersion films, to substrates (speed maximum 200 m/min).

Setting the operating speed of the coating plant to at least about 400 m/min has both economic and technical advantages. Preferably, the operating speed is at least about 750 m/min, especially preferably at least about 1000 m/min, and very especially preferably at least about 1500 m/min. It was especially surprising that, even at the latter speed, the heat-sensitive recording material obtained is not affected in any way, and the operation runs optimally even at this high speed.

In a preferred embodiment of the method according to the invention, the aqueous deaerated coating suspension has a viscosity of about 150 to about 800 mPas (Brookfield, 100 rpm, 20° C.). If the viscosity falls below the value of about 150 mPas or exceeds the value of about 800 mPas, this leads to poor runnability of the coating mass at the coating unit. The viscosity of the aqueous deaerated coating suspension is especially preferably about 200 to about 500 mPas.

In a preferred embodiment, the surface tension of the aqueous application suspension can be adjusted to about 25 to about 60 mN/m, preferably to about 35 to about 50 mN/m (measured according to the static ring method according to Du Noüy, DIN 53914), in order to optimise the method.

The heat sensitive colour-forming layer can be formed on-line or in a separate coating process off-line. This also applies to any subsequently applied layers or intermediate layers.

It is advantageous if the dried heat-sensitive colour-forming layer is subjected to a smoothing measure. It is advantageous here to adjust the Bekk smoothness, measured according to ISO 5627:1995-03, to between about 100 and about 1000 sec., preferably to between about 250 and about 600 sec.

The surface roughness (PPS) according to ISO 8791-4: 2008-05 is in the range of from about 0.50 to about 2.50 µm, especially preferably in the range of from about 1.00 to about 2.00 µm.

The preferred embodiments listed in conjunction with the compound of formula (I) also apply to the method for producing the heat-sensitive recording material according to the invention.

The present invention also relates to a heat-sensitive recording material obtainable by the above-mentioned method.

The method described above is advantageous from an economic point of view and allows a high process performance of the coating plant even at a speed of more than 1500 m/min without any impairment of the process product, that is to say the heat-sensitive recording material according to the invention. The method can be carried out on-line and off-line, which results in a desirable flexibility.

The heat-sensitive recording material according to the invention is phenol-free and well suited for POS (point-of-sale), label and/or ticket applications. It is also suitable for the production of parking tickets, travel tickets, admission tickets, lottery and betting tickets etc., which can be printed using the direct thermal process and require high resistance of the images recorded on them also under long-term storage, even under harsh climatic conditions with regard to temperature and ambient humidity.

Surprisingly, it has been shown that, using the colour developers of formula (I) according to the invention it is possible to provide heat-sensitive recording materials which are characterised especially in that they do not lose practically any of their ability to produce high image densities, even after weeks of storage of the unprinted materials even in high ambient humidity and/or at high temperature. The heat-sensitive recording materials according to the invention therefore show a surprisingly long storage capability.

The invention is explained in detail below on the basis of non-limiting examples.

EXAMPLES

Production of the compounds of formula (I) according to the invention.
Step A—Production of the Dinitro Sulfonates (According to JP 2014 094 888 A)

A solution of 60 mmol of the corresponding nitrobenzenesulfonyl chloride in 15 mL THF is added dropwise at room temperature with stirring to a solution of 60 mmol of the corresponding nitrophenol and 84 mmol triethylamine in 20 mL THF. The reaction solution is stirred for two hours at room temperature and then mixed with 65 mL water. The suspension is stirred for three hours at room temperature and then filtered. The residue is then washed with 10 mL water (3 to 6 times). The dinitro sulfonates were used in step B without further purification.

Step B—Reduction of the Nitro Groups to Primary Amines 0.420 mol $SnCl_2 \cdot 2H_2O$ is added (in portions) at room temperature with stirring to a solution of 0.060 mol of the product from step A in 200 mL ethyl acetate. The reaction solution is refluxed. The course of the reaction is monitored by means of thin-film chromatography (eluents:cyclohexane/ethyl acetate 1:1). Once the reaction is complete (about 2 to 3 h), 200 mL of a 50% aqueous potassium carbonate solution are added and the mixture is stirred for 30 min at room temperature. The phases are separated from one another. The aqueous phase is extracted with 100 mL ethyl acetate. The purified organic phases are dried over magnesium sulfate. The solvent is removed in a vacuum. The diamino sulfonates are used in step C without further purification.

Step C—Production of the Bis-Urea Compounds.

A solution of 15.2 mmol of the corresponding isocyanate in 25 mL ethyl acetate is added dropwise at room temperature with stirring to a solution of 7.6 mmol of the product from step B in 40 mL ethyl acetate. The reaction mixture is refluxed. The reaction mixture is refluxed and the progress of the reaction is monitored by means of HPLC. Once the reaction is complete, the precipitated bis-urea is filtered off, washed with 10 mL ethyl acetate (3 times), and dried in a vacuum. A further purification is possibly performed by recrystallisation from ethyl acetate or dichloromethane. In some cases the reaction solution is concentrated in a vacuum and the crystallisation is triggered by addition of a few drops of n-hexane.

The starting compounds are commercially obtainable.

Table 2 summarises the compounds of formula (I) produced here for the first time.

TABLE 2

Composition of compounds of formula (1) produced for the first time

| | Arrangement of $Ar^1$—NH—CO—NH— and $Ar^2$—NH—CO—NH— on the —$C_6H_4$—$SO_2$—O—$C_6H_4$ group | $Ar^1$ | $Ar^2$ |
|---|---|---|---|
| I | 2,3' | $C_6H_5$ | $C_6H_5$ |
| II | 2,4' | $C_6H_5$ | $C_6H_5$ |
| III | 3,2' | $C_6H_5$ | $C_6H_5$ |
| IV | 3,3' | $C_6H_5$ | $C_6H_5$ |
| V | 3,4' | $C_6H_5$ | $C_6H_5$ |
| VI | 4,2' | $C_6H_5$ | $C_6H_5$ |
| VII | 4,3' | $C_6H_5$ | $C_6H_5$ |
| VIII | 4,4' | $C_6H_5$ | $C_6H_5$ |
| IX | 4,3' | 2-$CH_3$—$C_6H_4$ | 2-$CH_3$—$C_6H_4$ |
| X | 4,3' | 3-$CH_3$—$C_6H_4$ | 3-$CH_3$—$C_6H_4$ |
| XI | 4,3' | 4-$CH_3$—$C_6H_4$ | 4-$CH_3$—$C_6H_4$ |
| XII | 4,3' | 2,4,6-tri$CH_3$—$C_6H_2$ | 2,4,6-tri$CH_3$—$C_6H_2$ |
| XIII | 4,3' | 1-Naph | 1-Naph |
| XIV | 4,3' | 4-$CH_3O$—$C_6H_4$ | 4-$CH_3O$—$C_6H_4$ |
| XV | 4,3' | 4-Cl—$C_6H_4$ | 4-Cl—$C_6H_4$ |
| XVI | 4,3' | 4-F—$C_6H_4$ | 4-F—$C_6H_4$ |
| XVII | 4,3' | 4-$CH_3CO$—$C_6H_4$ | 4-$CH_3CO$—$C_6H_4$ |
| XVIII | 4,3' | 4-($CO_2C_2H_5$)—$C_6H_4$ | 4-($CO_2C_2H_5$)—$C_6H_4$ |
| XIX | 4,3' | 4-CN—$C_6H_4$ | 4-CN—$C_6H_4$ |
| XX | 4,3' | 4-$NO_2$—$C_6H_4$ | 4-$NO_2$—$C_6H_4$ |
| XXI | 4,3' | 4-$CH_3O$—$C_6H_4$ | 4-$NO_2$—$C_6H_4$ |
| XXII | 4,3' | 4-$NO_2$—$C_6H_4$ | 4-$CH_3O$—$C_6H_4$ |

Analytical Data:

I, $C_{26}H_{22}N_4O_5S$, M=502.5, 3'-(3'-phenylureido)phenyl 2-(3-phenylureido)benzenesulfonate MS (ESI): m/z (%)=503.1 (100) [M+H]$_+$.

$^1$H-NMR (500 MHz, DMSO-$d_6$): δ (ppm)=9.88 (1H, s), 8.82 (1H, s), 8.63 (1H, s), 8.43 (1H, s), 8.17-8.16 (1H, m), 7.75-7.70 (2H, m), 7.53-7.51 (2H, m), 7.46-7.43 (3H, m), 7.32-7.26 (5H, m), 7.23-7.20 (2H, m), 7.03-6.97 (2H, m), 6.55 (1H, ddd, J=8.0, 2.4, 1.0 Hz).

$^{13}$C-NMR (126 MHz, DMSO-$d_6$): δ (ppm)=152.13 (NHCONH), 151.80 (NHCONH), 149.06, 141.21, 139.25, 139.25, 137.88, 135.43, 129.94, 129.87, 128.71, 128.66, 124.57, 122.82, 122.69, 122.31, 122.00, 118.60, 118.34, 116.89, 114.27, 111.37.

II, $C_{26}H_{22}N_4O_5S$, M=502.5, 4'-(3'-phenylureido)phenyl 2-(3-phenylureido)benzenesulfonate MS (ESI): m/z (%)=503.1 (100) [M+H]$_+$.

$^1$H-NMR (500 MHz, DMSO-$d_6$): δ (ppm)=9.88 (1H, s), 8.73 (1H, s), 8.63 (1H, s), 8.42 (1H, s), 8.13 (1H, dd, J=8.4, 1.0 Hz), 7.76-7.72 (1H, m), 7.66 (1H, dd, J=8.1, 1.5 Hz), 7.52-7.50 (2H, m), 7.43-7.40 (4H, m), 7.32-7.29 (2H, m), 7.28-7.25 (2H, m), 7.22-7.19 (1H, m), 7.02-6.99 (1H, m), 6.98-6.93 (3H, m).

$^{13}$C-NMR (126 MHz, DMSO-$d_6$): δ (ppm)=152.25 (NHCONH), 151.88 (NHCONH), 142.82, 139.37, 139.23, 138.99, 137.83, 135.39, 130.04, 128.73, 128.64, 124.83, 122.92, 122.80, 122.32, 122.14, 121.89, 118.96, 118.58, 118.25.

III, $C_{26}H_{22}N_4O_5S$, M=502.5, 2'-(3'-phenylureido)phenyl 3-(3-phenylureido)benzenesulfonate MS (ESI): m/z (%)=503.2 (100) [M+H]$_+$.

$^1$H-NMR (500 MHz, DMSO-$d_6$): δ (ppm)=9.05 (1H, s), 8.98 (1H, s), 8.60 (1H, s), 8.27-8.27 (1H, m), 8.19 (1H, s), 8.03 (1H, dd, J=8.3, 1.3 Hz), 7.54-7.52 (1H, m), 7.43-7.37 (6H, m), 7.30-7.27 (2H, m), 7.24-7.19 (3H, m), 7.13 (1H, dd, J=8.2, 1.2 Hz), 7.01-6.97 (2H, m), 6.96-6.93 (1H, m).

$^{13}$C-NMR (126 MHz, DMSO-$d_6$): δ (ppm)=152.08 (NHCONH), 151.53 (NHCONH), 140.66, 139.32, 139.10, 138.10, 134.47, 132.13, 129.67, 128.63, 128.58, 127.45, 123.73, 122.11, 122.07, 122.03, 121.81, 121.13, 121.03, 118.43, 118.05, 116.91.

IV, $C_{26}H_{22}N_4O_5S$, M=502.5, 3'-(3'-phenylureido)phenyl 3-(3-phenylureido)benzenesulfonate MS (ESI): m/z (%)=503.1 (100) [M+H]$_+$.

$^1$H-NMR (500 MHz, DMSO-$d_6$): δ (ppm)=9.13 (1H, s), 8.86 (1H, s), 8.73 (1H, s), 8.62 (1H, s), 8.23-8.22 (1H, m), 7.72 (1H, ddd, J=8.2, 2.2, 1.0 Hz), 7.58-7.55 (1H, m), 7.48-7.42 (6H, m), 7.31-7.25 (6H, m), 7.00 (1H, tt, J=7.4, 1.1 Hz), 6.98 (1H, tt, J=7.4, 1.1 Hz), 6.62 (1H, ddd, J=7.6, 2.3, 1.6 Hz).

$^{13}$C-NMR (126 MHz, DMSO-$d_6$): δ (ppm)=152.30 (NHCONH), 152.18 (NHCONH), 149.34, 141.17, 140.91, 139.27, 139.11, 135.07, 130.09, 129.86, 128.68, 128.67, 123.76, 122.22, 122.01, 120.87, 118.59, 118.37, 116.67, 116.61, 114.58, 111.38.

V, $C_{26}H_{22}N_4O_5S$, M=502.5, 4'-(3'-phenylureido)phenyl 3-(3-phenylureido)benzenesulfonate MS (ESI): m/z (%)=503.1 (100) [M+H]$_+$.

$^1$H-NMR (500 MHz, DMSO-$d_6$): δ (ppm)=9.13 (1H, s), 8.76 (1H, s), 8.74 (1H, s), 8.63 (1H, s), 8.19-8.19 (1H, m), 7.72 (1H, ddd, J=8.2, 2.2, 1.0 Hz), 7.58-7.55 (1H, m), 7.48-7.42 (6H, m), 7.41 (1H, ddd, J=7.8, 1.8, 1.0 Hz), 7.31-7.25 (4H, m), 7.01-6.95 (4H, m).

$^{13}$C-NMR (126 MHz, DMSO-$d_6$): δ (ppm)=152.34 (NHCONH), 152.33 (NHCONH), 143.22, 140.88, 139.40, 139.12, 138.78, 134.97, 130.06, 128.69, 128.67, 123.76, 122.31, 122.24, 121.92, 120.99, 119.04, 118.62, 118.30, 116.74.

VI, $C_{26}H_{22}N_4O_5S$, M=502.5, 2'-(3'-phenylureido)phenyl 4-(3-phenylureido)benzenesulfonate MS (ESI): m/z (%)=503.1 (100) [M+H]$_+$.

$^1$H-NMR (500 MHz, DMSO-d$_6$): δ (ppm)=9.15 (1H, s), 9.10 (1H, s), 8.71 (1H, s), 8.13 (1H, s), 8.05 (1H, dd, J=8.3, 1.5 Hz), 7.75-7.74 (2H, m), 7.60-7.58 (2H, m), 7.44-7.42 (2H, m), 7.42-7.40 (2H, m), 7.31-7.21 (5H, m), 7.14 (1H, dd, J=8.2, 1.4 Hz), 7.02-6.97 (2H, m), 6.95-6.92 (1H, m).

$^{13}$C-NMR (126 MHz, DMSO-d$_6$): δ (ppm)=151.71 (NH$\underline{C}$ONH), 151.62 (NH$\underline{C}$ONH), 145.83, 139.25, 138.91, 138.07, 132.15, 129.83, 128.68, 128.63, 127.30, 125.32, 122.32, 122.18, 122.01, 121.90, 120.94, 118.54, 118.29, 117.19.

VII, $C_{26}H_{22}N_4O_5S$, M=502.5, 3'-(3'-phenylureido)phenyl 4-(3-phenylureido)benzenesulfonate MS (ESI): m/z (%)=503.1 (100) [M+H]$_+$.

$^1$H-NMR (500 MHz, DMSO-d$_6$): δ (ppm)=9.28 (1H, s), 8.84 (1H, s), 8.81 (1H, s), 8.62 (1H, s), 7.79-7.77 (2H, m), 7.72-7.71 (2H, m), 7.48-7.46 (2H, m), 7.45-7.43 (2H, m), 7.38-7.38 (1H, m), 7.32-7.24 (6H, m), 7.03-7.00 (1H, m), 6.98-6.95 (1H, m), 6.60-6.59 (1H, m).

$^{13}$C-NMR (126 MHz, DMSO-d$_6$): δ (ppm)=152.16 (NH$\underline{C}$ONH), 151.93 (NH$\underline{C}$ONH), 149.43, 145.61, 141.08, 139.27, 138.94, 129.76, 129.56, 128.71, 128.64, 125.98, 122.36, 121.96, 118.56, 118.35, 117.60, 116.51, 114.74, 111.47.

VIII, $C_{26}H_{22}N_4O_5S$, M=502.5, 4'-(3'-phenylureido)phenyl 4-(3-phenylureido)benzenesulfonate MS (ESI): m/z (%)=503.2 (100) [M+H]$_+$.

$^1$H-NMR (500 MHz, DMSO-d$_6$): δ (ppm)=9.28 (1H, s), 8.82 (1H, s), 8.74 (1H, s), 8.63 (1H, s), 7.75-7.73 (2H, m), 7.71-7.70 (2H, m), 7.48-7.47 (2H, m), 7.44-7.43 (4H, m), 7.32-7.29 (2H, m), 7.29-7.25 (2H, m), 7.03-7.00 (1H, m), 6.98-6.96 (1H, m), 6.96-6.92 (2H, m).

$^{13}$C-NMR (126 MHz, DMSO-d$_6$): δ (ppm)=152.32 (NH$\underline{C}$ONH), 151.94 (NH$\underline{C}$ONH), 145.56, 143.28, 139.40, 138.95, 138.63, 129.62, 128.72, 128.64, 125.89, 122.39, 122.37, 121.87, 118.96, 118.57, 118.26, 117.58.

IX, $C_{28}H_{26}N_4O_5S$, M=530.6, 3'-(3'-(2'-tolyl)ureido)phenyl 4-(3-(2-tolyl)ureido)benzenesulfonate MS (ESI): m/z (%)=531.1 (100) [M+H]$_+$.

$^1$H-NMR (500 MHz, DMSO-d$_6$): δ (ppm)=9.58 (1H, s), 9.17 (1H, s), 8.09 (1H, s), 7.90 (1H, s), 7.79-7.76 (4H, m), 7.73-7.70 (2H, m), 7.40-7.39 (1H, m), 7.31-7.28 (1H, m), 7.27-7.24 (1H, m), 7.20-7.12 (4H, m), 7.01-6.98 (1H, m), 6.97-6.93 (1H, m), 6.59 (1H, ddd, J=7.7, 2.4, 1.4 Hz), 2.25 (3H, s), 2.23 (3H, s).

$^{13}$C-NMR (126 MHz, DMSO-d$_6$): δ (ppm)=152.31 (NH$\underline{C}$ONH), 152.11 (NH$\underline{C}$ONH), 149.46, 145.75, 141.25, 136.96, 136.61, 130.15, 130.06, 129.81, 129.61, 128.35, 127.88, 126.07, 126.03, 125.84, 123.37, 122.91, 121.70, 121.36, 117.44, 116.29, 114.63, 111.29, 17.68 ($\underline{C}$H$_3$), 17.68 ($\underline{C}$H$_3$).

X, $C_{28}H_{26}N_4O_5S$, M=530.6, 3'-(3'-(3'-tolyl)ureido)phenyl 4-(3-(3-tolyl)ureido)benzenesulfonate MS (ESI): m/z (%)=531.1 (100) [M+H]$_+$.

$^1$H-NMR (500 MHz, DMSO-d$_6$): δ (ppm)=9.26 (1H, s), 8.83 (1H, s), 8.73 (1H, s), 8.54 (1H, s), 7.78-7.76 (2H, m), 7.72-7.70 (2H, m), 7.40-7.39 (1H, m), 7.31-7.31 (1H, m), 7.29-7.21 (5H, m), 7.19-7.13 (2H, m), 6.84-6.82 (1H, m), 6.80-6.78 (1H, m), 6.59 (1H, ddd, J=7.6, 2.4, 1.5 Hz), 2.29 (3H, s), 2.27 (3H, s).

$^{13}$C-NMR (126 MHz, DMSO-d$_6$): δ (ppm)=152.14 (NH$\underline{C}$ONH), 151.90 (NH$\underline{C}$ONH), 149.43, 145.63, 141.12, 139.19, 138.86, 137.94, 137.86, 129.75, 129.55, 128.55, 128.49, 125.95, 123.11, 122.72, 119.08, 118.85, 117.58, 116.47, 115.74, 115.53, 114.69, 111.44, 21.07 ($\underline{C}$H$_3$), 21.07 ($\underline{C}$H$_3$).

XI, $C_{28}H_{26}N_4O_5S$, M=530.6, 3'-(3'-(4'-tolyl)ureido)phenyl 4-(3-(4-tolyl)ureido)benzenesulfonate MS (ESI): m/z (%)=531.1 (100) [M+H]$_+$.

$^1$H-NMR (500 MHz, DMSO-d$_6$): δ (ppm)=9.23 (1H, s), 8.79 (1H, s), 8.71 (1H, s), 8.50 (1H, s), 7.77-7.75 (2H, m), 7.71-7.70 (2H, m), 7.37-7.35 (3H, m), 7.33-7.31 (2H, m), 7.26-7.23 (2H, m), 7.11-7.10 (2H, m), 7.07-7.05 (2H, m), 6.60-6.57 (1H, m), 2.25 (3H, s), 2.21 (3H, s).

$^{13}$C-NMR (126 MHz, DMSO-d$_6$): δ (ppm)=152.18 (NH$\underline{C}$ONH), 151.94 (NH$\underline{C}$ONH), 149.44, 145.72, 141.18, 136.69, 136.38, 131.29, 130.82, 129.73, 129.56, 129.11, 129.05, 125.85, 118.65, 118.44, 117.53, 116.43, 114.66, 111.41, 20.24 ($\underline{C}$H$_3$), 20.19 ($\underline{C}$H$_3$).

XII, $C_{32}H_{34}N_4O_5S$, M=586.7, 3'-(3'-(2',4',6'-trimethylphenyl)ureido)phenyl 4-(3-(2,4,6-trimethylphenyl)ureido)benzenesulfonate MS (ESI): m/z (%)=587.2 (100) [M+H]$_+$.

$^1$H-NMR (500 MHz, DMSO-d$_6$): δ (ppm)=9.34 (1H, s), 8.86 (1H, s), 7.82 (1H, s), 7.73-7.71 (2H, m), 7.69-7.67 (2H, m), 7.61 (1H, s), 7.35-7.35 (1H, m), 7.29-7.28 (1H, m), 7.23-7.20 (1H, m), 6.90-6.87 (4H, m), 6.54-6.53 (1H, m), 2.23 (3H, s), 2.23 (3H, s), 2.17 (6H, s), 2.14 (6H, s).

$^{13}$C-NMR (126 MHz, DMSO-d$_6$): δ (ppm)=152.90 (NH$\underline{C}$ONH), 152.59 (NH$\underline{C}$ONH), 149.42, 146.17, 141.73, 135.24, 135.22, 135.20, 134.94, 132.29, 131.99, 129.62, 129.49, 128.26, 128.19, 125.50, 117.25, 116.19, 114.21, 111.23, 20.37 ($\underline{C}$H$_3$), 17.98 ($\underline{C}$H$_3$).

XIII, $C_{34}H_{26}N_4O_5S$, M=602.7, 3'-(3'-(1'-naphthyl)ureido)phenyl 4-(3-(1-naphthyl)ureido)benzenesulfonate MS (ESI): m/z (%)=603.2 (100) [M+H]$_+$.

$^1$H-NMR (500 MHz, DMSO-d$_6$): δ (ppm)=9.64 (1H, s), 9.23 (1H, s), 8.91 (1H, s), 8.75 (1H, s), 8.12-8.09 (2H, m), 7.99-7.96 (2H, m), 7.95-7.94 (1H, m), 7.92-7.91 (1H, m), 7.83-7.81 (2H, m), 7.79-7.77 (2H, m), 7.70-7.68 (1H, m), 7.64-7.62 (1H, m), 7.61-7.45 (7H, m), 7.35 (1H, ddd, J=8.2, 2.0, 1.1 Hz), 7.31-7.28 (1H, m), 6.63 (1H, ddd, J=8.0, 2.4, 1.0 Hz).

$^{13}$C-NMR (126 MHz, DMSO-d$_6$): δ (ppm)=152.63 (NH$\underline{C}$ONH), 152.48 (NH$\underline{C}$ONH), 149.51, 145.70, 141.18, 133.90, 133.64, 133.62, 133.58, 129.90, 129.69, 128.32, 128.30, 126.32, 126.08, 126.00, 125.90, 125.80, 125.78, 125.73, 125.70, 125.65, 123.70, 123.19, 121.33, 121.25, 118.34, 117.81, 117.62, 116.47, 114.82, 111.44.

XIV, $C_{28}H_{26}N_4O_7S$, M=562.6, 3'-(3'-(4'-methoxyphenyl)ureido)phenyl 4-(3-(4-methoxyphenyl)ureido)benzenesulfonate MS (ESI): m/z (%)=563.2 (100) [M+H]$_+$.

$^1$H-NMR (500 MHz, DMSO-d$_6$): δ (ppm)=9.21 (1H, s), 8.76 (1H, s), 8.63 (1H, s), 8.42 (1H, s), 7.77-7.74 (2H, m), 7.71-7.69 (2H, m), 7.39-7.32 (5H, m), 7.28-7.22 (2H, m), 6.90-6.87 (2H, m), 6.87-6.84 (2H, m), 6.58 (1H, ddd, J=7.4, 2.3, 1.7 Hz), 3.73 (3H, s), 3.69 (3H, s).

$^{13}$C-NMR (126 MHz, DMSO-d$_6$): δ (ppm)=154.89, 154.61, 152.34 (NH$\underline{C}$ONH), 152.09 (NH$\underline{C}$ONH), 149.44, 145.81, 141.28, 132.28, 131.92, 129.71, 129.55, 125.74, 120.45, 120.23, 117.48, 116.39, 114.55, 113.99, 113.92, 111.37, 55.14 (O$\underline{C}$H$_3$), 55.07 (O$\underline{C}$H$_3$).

XV, $C_{26}H_{20}Cl_2N_4O_5S$, M=571.4, 3'-(3'-(4'-chlorophenyl)ureido)phenyl 4-(3-(4-chlorophenyl)ureido)benzenesulfonate MS (ESI): m/z (%)=571.0 (100) [M+H]$_+$.

$^1$H-NMR (500 MHz, DMSO-d$_6$): δ (ppm)=9.31 (1H, s), 8.95 (1H, s), 8.87 (1H, s), 8.76 (1H, s), 7.78-7.76 (2H, m), 7.72-7.69 (2H, m), 7.51-7.48 (2H, m), 7.48-7.45 (2H, m), 7.37-7.36 (1H, m), 7.36-7.33 (2H, m), 7.31-7.28 (2H, m), 7.28-7.25 (2H, m), 6.61 (1H, ddd, J=6.0, 3.1, 2.4 Hz).

$^{13}$C-NMR (126 MHz, DMSO-$d_6$): δ (ppm)=152.05 (NH$\underline{C}$ONH), 151.86 (NH$\underline{C}$ONH), 149.41, 145.45, 140.88, 138.29, 137.96, 129.77, 129.56, 128.57, 128.47, 126.13, 126.00, 125.55, 120.09, 119.84, 117.74, 116.62, 114.94, 111.58.

XVI, $C_{26}H_{20}F_2N_4O_5S$, M=538.5, 3'-(3'-(4'-fluorophenyl)ureido)phenyl 4-(3-(4-fluorophenyl)ureido)benzenesulfonate MS (ESI): m/z (%)=539.2 (100) [M+H]$_+$.

$^1$H-NMR (500 MHz, DMSO-$d_6$): δ (ppm)=9.28 (1H, s), 8.85 (1H, s), 8.84 (1H, s), 8.65 (1H, s), 7.78-7.75 (2H, m), 7.72-7.69 (2H, m), 7.50-7.42 (4H, m), 7.37-7.36 (1H, m), 7.29-7.23 (2H, m), 7.16-7.06 (4H, m), 6.60 (1H, ddd, J=7.5, 2.3, 1.6 Hz).

$^{13}$C-NMR (126 MHz, DMSO-$d_6$): δ (ppm)=158.49 (d, J=29.7 Hz), 156.59 (d, J=29.3 Hz), 152.26 (NH$\underline{C}$ONH), 152.05 (NH$\underline{C}$ONH), 149.43, 145.60, 141.06, 135.60 (d, J=2.3 Hz), 135.26 (d, J=2.3 Hz), 129.75, 129.56, 126.01, 120.45 (d, J=7.8 Hz), 120.17 (d, J=7.7 Hz), 117.65, 116.56, 115.27 (d, J=13.4 Hz), 115.10 (d, J=13.4 Hz), 114.78, 111.52.

XVII, $C_{30}H_{26}N_4O_7S$, M=586.6, 3'-(3'-(4'-acetylphenyl)ureido)phenyl 4-(3-(4-acetylphenyl)ureido)benzenesulfonate MS (ESI): m/z (%)=587.1 (100) [M+H]$_+$.

$^1$H-NMR (500 MHz, DMSO-$d_6$): δ (ppm)=9.41 (1H, s), 9.24 (1H, s), 9.06 (1H, s), 8.98 (1H, s), 7.92-7.91 (2H, m), 7.89-7.87 (2H, m), 7.80-7.78 (2H, m), 7.74-7.73 (2H, m), 7.60-7.59 (2H, m), 7.57-7.56 (2H, m), 7.38-7.38 (1H, m), 7.28-7.27 (2H, m), 6.65-6.63 (1H, m), 2.52 (3H, s), 2.46 (3H, s).

$^{13}$C-NMR (126 MHz, DMSO-$d_6$): δ (ppm)=196.23 ($\underline{C}$OCH$_3$), 196.14 ($\underline{C}$OCH$_3$), 151.83 (NH$\underline{C}$ONH), 151.69 (NH$\underline{C}$ONH), 149.43, 145.29, 143.94, 143.58, 140.69, 130.95, 130.61, 129.89, 129.66, 129.54, 129.51, 126.34, 117.94, 117.51, 117.27, 116.81, 115.27, 111.75, 26.26 ($\underline{C}$H$_3$), 26.17 ($\underline{C}$H$_3$).

XVIII, $C_{32}H_{30}N_4O_9S$, M=646.7, ethyl 4-(3-(4-((3-(3-(4-(ethoxycarbonyl)phenyl)ureido)phenoxy)sulfonyl)phenyl)ureido)benzoate MS (ESI): m/z (%)=647.2 (100) [M+H]$_+$.

$^1$H-NMR (500 MHz, DMSO-$d_6$): δ (ppm)=9.38 (1H, s), 9.21 (1H, s), 9.03 (1H, s), 8.95 (1H, s), 7.91-7.89 (2H, m), 7.88-7.86 (2H, m), 7.80-7.77 (2H, m), 7.74-7.72 (2H, m), 7.60-7.58 (2H, m), 7.58-7.55 (2H, m), 7.38-7.37 (1H, m), 7.28-7.27 (2H, m), 6.66-6.63 (1H, m), 4.29 (2H, q, J=7.1 Hz), 4.26 (2H, q, J=7.1 Hz), 1.31 (3H, q, J=7.1 Hz), 1.29 (3H, q, J=7.1 Hz).

$^{13}$C-NMR (126 MHz, DMSO-$d_6$): δ (ppm)=165.27 ($\underline{C}$OO), 165.26 ($\underline{C}$OO), 151.79 (NH$\underline{C}$ONH), 151.65 (NH$\underline{C}$ONH), 149.40, 145.26, 143.87, 143.52, 140.65, 130.21, 130.20, 129.82, 129.59, 126.35, 123.34, 122.96, 117.90, 117.61, 117.36, 116.75, 115.22, 111.71, 60.21, 60.13 ($\underline{C}$H$_2$), 14.11 ($\underline{C}$H$_3$).

XIX, $C_{28}H_{20}N_6O_5S$, M=552.6, 3'-(3'-(4'-cyanophenyl)ureido)phenyl 4-(3-(4-cyanophenyl)ureido)benzenesulfonate MS (ESI): m/z (%)=553.1 (100) [M+H]$_+$.

$^1$H-NMR (500 MHz, DMSO-d): δ (ppm)=9.45 (1H, s), 9.32 (1H, s), 9.14 (1H, s), 9.02 (1H, s), 7.80-7.77 (2H, m), 7.76-7.71 (4H, m), 7.70-7.67 (2H, m), 7.65-7.63 (2H, m), 7.62-7.60 (2H, m), 7.36-7.36 (1H, m), 7.28-7.27 (2H, m), 6.66-6.63 (1H, m).

$^{13}$C-NMR (126 MHz, DMSO-$d_6$): δ (ppm)=151.74 (NH$\underline{C}$ONH), 151.62 (NH$\underline{C}$ONH), 149.37, 145.10, 143.79, 143.45, 140.50, 133.20, 133.10, 129.88, 129.61, 126.50, 119.05, 119.03, 118.36, 118.13, 118.01, 116.88, 115.37, 111.80, 103.95, 103.46.

XX, $C_{26}H_{20}N_6O_9S$, M=592.5, 3'-(3'-(4'-nitrophenyl)ureido)phenyl 4-(3-(4-nitrophenyl)ureido)benzenesulfonate MS (ESI): m/z (%)=593.1 (100) [M+H]$_+$.

$^1$H-NMR (500 MHz, DMSO-$d_6$): δ (ppm)=9.52 (1H, s), 9.48 (1H, s), 9.36 (1H, s), 9.06 (1H, s), 8.20-8.17 (2H, m), 8.15-8.12 (2H, m), 7.81-7.78 (2H, m), 7.75-7.73 (2H, m), 7.70-7.64 (4H, m), 7.37-7.36 (1H, m), 7.31-7.27 (2H, m), 6.69-6.66 (1H, m).

$^{13}$C-NMR (126 MHz, DMSO-$d_6$): δ (ppm)=151.60 (NH$\underline{C}$ONH), 151.51 (NH$\underline{C}$ONH), 149.38, 145.93, 145.54, 145.00, 141.46, 141.12, 140.36, 129.88, 129.62, 126.64, 124.93, 124.90, 118.13, 117.79, 117.53, 116.97, 115.57, 111.91.

XXI, $C_{27}H_{23}N_5O_8S$, M=577.6, 3'-(3'-(4'-nitrophenyl)ureido)phenyl 4-(3-(4-methoxyphenyl)ureido)benzenesulfonate MS (ESI): m/z (%)=578.1 (100) [M+H]$_+$.

$^1$H-NMR (500 MHz, DMSO-$d_6$): δ (ppm)=9.37 (1H, s), 9.20 (1H, s), 9.07 (1H, s), 8.62 (1H, s), 8.18-8.15 (2H, m), 7.76-7.74 (2H, m), 7.71-7.66 (4H, m), 7.37-7.34 (3H, m), 7.31-7.27 (2H, m), 6.89-6.86 (2H, m), 6.67-6.65 (1H, m), 3.72 (3H, s).

$^{13}$C-NMR (126 MHz, DMSO-$d_6$): δ (ppm)=154.89, 152.08 (NH$\underline{C}$ONH), 151.64 (NH$\underline{C}$ONH), 149.42, 145.94, 145.87, 141.17, 140.36, 131.88, 129.87, 129.57, 125.63, 124.94, 120.44, 117.59, 117.51, 116.95, 115.56, 113.97, 111.94, 55.13 (O$\underline{C}$H$_3$).

XXII, $C_{27}H_{23}N_5O_8S$, M=577.6, 3'-(3'-(4'-methoxyphenyl)ureido)phenyl 4-(3-(4-nitrophenyl)ureido)benzenesulfonate MS (ESI): m/z (%)=578.1 (100) [M+H]$_+$.

$^1$H-NMR (500 MHz, DMSO-$d_6$): δ (ppm)=9.52 (2H, s), 8.75 (1H, s), 8.42 (1H, s), 8.22-8.19 (2H, m), 7.81-7.79 (2H, m), 7.75-7.73 (2H, m), 7.73-7.70 (2H, m), 7.37-7.36 (1H, m), 7.35-7.31 (2H, m), 7.26-7.22 (2H, m), 6.86-6.82 (2H, m), 6.60-6.56 (1H, m), 3.68 (3H, s).

$^{13}$C-NMR (126 MHz, DMSO-$d_6$): δ (ppm)=154.60, 152.33 (NH$\underline{C}$ONH), 151.55 (NH$\underline{C}$ONH), 149.41, 145.61, 144.94, 141.47, 141.30, 132.28, 129.73, 129.60, 126.77, 124.98, 120.20, 118.11, 117.86, 116.43, 114.53, 113.91, 111.34, 55.07 (O$\underline{C}$H$_3$).

Non-phenolic colour developers from the prior art were used as comparative developers, specifically N-(2-(3-phenylureido)phenyl)benzene-sulfonamide (NKK 1304, Nippon Soda) and a sulfonylurea, Pergafast 201®, (PF 201, BASF).

An aqueous coating suspension was applied to one side of a 63 g/m$^2$ synthetic base paper (Yupo® FP680) using a doctor bar on a laboratory scale to form the heat-sensitive colour-forming layer of a heat-sensitive recording paper. After drying, a thermal recording sheet was obtained. The application rate of the heat-sensitive colour-forming layer was between 3.8 and 4.2 g/m$^2$.

On the basis of the above information, a heat-sensitive recording material or thermal paper was produced, with the following formulations of aqueous application suspensions being used to form a composite structure on a carrier substrate, and then the other layers, especially a protective layer, being formed in the usual manner, which will not be discussed separately here.

Production of the dispersions (in each case for 1 part by weight) for the application suspensions The aqueous dispersion A (colour former dispersion) is produced by grinding 20 parts by weight of 3-N-n-dibutylamino-6-methyl-7-anilinofluoran (ODB-2) with 33 parts by weight of a 15% aqueous solution of Ghosenex™ L-3266 (sulfonated polyvinyl alcohol, Nippon Ghosei) in a bead mill.

The aqueous dispersion B (colour developer dispersion) is produced by grinding 40 parts by weight of the colour developer together with 66 parts by weight of a 15% aqueous solution of Ghosenex™ L-3266 in a bead mill.

The aqueous dispersion C (sensitising agent dispersion) is produced by grinding 40 parts by weight of 1,2-diphenoxyethane with 33 parts by weight of a 15% aqueous solution of Ghosenex™ L-3266 in a bead mill.

All dispersions produced by grinding have an average particle size $D_{(4.3)}$ of 0.80-1.20 µm. The particle size distribution of the dispersions was measured by laser diffraction using a Coulter LS230 instrument from Beckman Coulter.

Dispersion D (lubricant dispersion) is a 20% zinc stearate dispersion consisting of 9 parts by weight of Zn-stearate, 1 part by weight of Ghosenex™ L-3266, and 40 parts by weight of water.

Pigment P is a 72% coating kaolin suspension (Lustra® S, BASF).

The binder consists of a 10% aqueous polyvinyl alcohol solution (Poval 28-99, Kuraray Europe).

The heat-sensitive application suspension is produced by mixing, with stirring, 1 part of A, 1 part of B, 1 part of C, 56 parts of D, 146 parts of pigment P and 138 parts of binder solution (all parts by weight), taking into account the order of introduction B, D, C, P, A, binder, and bringing the mixture to a solids content of about 25% with water.

The heat-sensitive coating suspensions thus obtained were used to produce composite structures of paper carrier and thermal reaction layer.

The thermal recording materials were evaluated as below (see Tables 3, 4 and 5).

(1) Dynamic Colour Density:

The papers (6 cm wide strips) were thermally printed with a chessboard pattern with 10 energy levels using an Atlantek 200 test printer (Atlantek, USA) with a Kyocera print bar of 200 dpi and 560 ohms at an applied voltage of 20.6 V and a maximum pulse width of 0.8 ms. The image density (optical density, o.d.) was measured with a SpectroEye densitometer from X-Rite at an energy level of 0.45 mJ/dot. The measurement uncertainty of the o.d. values is estimated at 2%.

(2) Static Colour Density (Starting Temperature):

The recording sheet was pressed against a series of thermostatically controlled metallic stamps heated to different temperatures with a contact pressure of 0.2 kg/cm² and a contact time of 5 seconds (thermal tester TP 3000QM, Maschinenfabrik Hans Rychiger AG, Steffisburg, Switzerland). The image density (opt. density) of the images thus produced was measured with a SpectroEye densitometer from X-Rite.

The static starting point is, by definition, the lowest temperature at which an optical density of 0.2 is achieved. The accuracy of the measuring method was ≤±0.5° C.

(3) Resistance Test of the Printed Image a) Resistance Test of the Printed Image Under Artificial Ageing Conditions:

A sample of the thermal recording paper recorded dynamically in accordance with the method from (1) was stored for 7 days under each of the following conditions: i) 50° C. (dry ageing), ii) 40° C., 85% relative humidity (damp ageing) and iii) under artificial light from fluorescent tubes, illumination level 16000 Lux (light ageing).

Once the test time had passed, the image density was measured at an applied energy of 0.45 mJ/dot and was set in relation to the corresponding image density values prior to the artificial ageing in accordance with the formula (Eq. 1).

$$\% \text{ remaining image density} = \left(\frac{\text{image density after test}}{\text{image density before test}}\right) * 100 \quad \text{(Eq. 1)}$$

The spread of the % values calculated according to (Eq. 1) is ≤±2 percentage points.

b) Resistance to Plasticiser:

A plasticiser-containing plastic wrap (PVC film with 20 to 25% dioctyladipate) was brought into contact with the sample of thermal recording paper recorded dynamically in accordance with the method from (1), avoiding folds and inclusions of air, wound into a roll, and stored for 16 hours. A second sample was stored at 40° C. at room temperature (20 to 22° C.). Once the film had been removed, the image density (o.d.) was measured and set in relation with the corresponding image density values prior to the plasticiser influence in accordance with the formula (Eq. 1).

c) Resistance to Adhesive:

A strip of transparent tesa self-adhesive tape (Tesafilm® crystal-clear, #57315) and, separately, a strip of tesa packaging adhesive tape (#04204) were glued to the sample of thermal recording paper dynamically recorded in accordance with the method from (1), avoiding folds and inclusions of air. Following storage at room temperature (20 to 22° C.), the image density (o.d.) was measured after 24 hours and after 7 days—through the adhesive tape in question—and was set in relation to the image density values, determined in a similar way, of the freshly glued sample in accordance with the formula (Eq. 1).

4) Shelf Life of the Unprinted Thermal Paper:

A sheet of recording paper was cut into three identical strips. One strip was dynamically recorded according to the process of (1) and the image density was determined. The other two strips were stored in the unprinted (white) state for 4 weeks in a climate of a) 40° C. and 85% relative humidity (r. h.) and b) 60° C. and 50% relative humidity (r. h.).

After conditioning the papers at room temperature, they were dynamically printed in accordance with the method from (1) and the image density was determined using a densitometer at an applied energy of 0.45 mJ/dot. The remaining writing performance (%) of the stored samples in relation to the fresh (not aged) samples was calculated according to equation (Eq. 1).

Tables 3 to 5 summarise the evaluation of the recording materials produced.

TABLE 3

Image density, starting temperature and artificial ageing

| Colour developer | o.d. (0.45 mJ/dot) | Starting point (° C.) | Artificial ageing* | | |
|---|---|---|---|---|---|
| | | | dry | damp | light |
| III | 1.21 | 75 | 97 | 98 | 87 |
| IV | 1.28 | 81 | 100 | 98 | 87 |
| V | 1.25 | 87 | 99 | 100 | 91 |
| VII | 1.32 | 76 | 100 | 100 | 86 |
| VIII | 1.30 | 83 | 100 | 100 | 88 |
| X | 1.21 | 79 | 100 | 100 | 80 |

TABLE 3-continued

Image density, starting temperature and artificial ageing

| Colour developer | o.d. (0.45 mJ/dot) | Starting point (° C.) | Artificial ageing* | | |
|---|---|---|---|---|---|
| | | | dry | damp | light |
| XIV | 1.29 | 104 | 99 | 99 | 91 |
| XV | 1.32 | 85 | 97 | 100 | 87 |
| XVI | 1.30 | 86 | 98 | 99 | 88 |
| XVII | 1.32 | 83 | 97 | 99 | 77 |
| XVIII | 1.28 | 76 | 99 | 100 | 81 |
| XIX | 1.35 | 87 | 98 | 98 | 85 |
| XX | 1.28 | 78 | 99 | 100 | 84 |
| XXI | 1.27 | 77 | 97 | 98 | 88 |
| XXII | 1.30 | 76 | 97 | 98 | 86 |
| Comparative example NKK 1304 | 1.25 | 86 | 100 | 99 | 72 |
| Comparative example PF 201 | 1.21 | 77 | 99 | 97 | 70 |

*Percentage of remaining image density in accordance with Eq. 1

TABLE 4

Resistance of the printed image

| Colour developer | Tesa adhesive tape* | | | | Plasticiser film* | |
|---|---|---|---|---|---|---|
| | 24 h | | 7 days | | 16 h | |
| | #57315 | #04204 | #57315 | #04204 | R.T. | 40° C. |
| III | 67 | 42 | 29 | 22 | 94 | 73 |
| IV | 73 | 53 | 49 | 32 | 99 | 92 |
| V | 78 | 61 | 57 | 43 | 100 | 94 |
| VII | 82 | 62 | 56 | 34 | 99 | 90 |
| VIII | 83 | 69 | 67 | 49 | 98 | 91 |
| X | 74 | 61 | 49 | 40 | 98 | 86 |
| XIV | 81 | 72 | 56 | 33 | 89 | 26 |
| XV | 83 | 73 | 57 | 42 | 97 | 90 |
| XVI | 73 | 57 | 43 | 36 | 98 | 86 |
| XVII | 89 | 92 | 78 | 77 | 94 | 94 |
| XVIII | 75 | 65 | 45 | 38 | 99 | 89 |
| XIX | 85 | 84 | 68 | 64 | 98 | 90 |
| XX | 81 | 76 | 58 | 54 | 97 | 92 |
| XXI | 80 | 73 | 56 | 53 | 98 | 91 |
| XXII | 84 | 80 | 63 | 64 | 98 | 91 |
| Comparative example NKK 1304 | 40 | 18 | 10 | 10 | 76 | 15 |
| Comparative example PF 201 | 66 | 33 | 25 | 12 | 92 | 63 |

*Percentage of remaining image density in accordance with Eq. 1.

TABLE 5

Writing performance after storage

| Colour developer | o.d. prior to storage | 4 weeks 40° C./ 85% r.h. | | 4 weeks 60° C./ 50% r.h. | |
|---|---|---|---|---|---|
| | | o.d. after storage | remaining o.d.* (%) | o.d. after storage | remaining o.d.* (%) |
| III | 1.21 | 1.21 | 100 | 1.19 | 98 |
| IV | 1.28 | 1.28 | 100 | 1.25 | 98 |
| V | 1.25 | 1.25 | 100 | 1.24 | 99 |
| VII | 1.32 | 1.31 | 99 | 1.28 | 97 |
| VIII | 1.30 | 1.29 | 99 | 1.29 | 99 |
| X | 1.21 | 1.21 | 100 | 1.12 | 93 |
| XIV | 1.29 | 1.29 | 100 | 1.29 | 100 |
| XV | 1.32 | 1.32 | 100 | 1.32 | 100 |
| XVI | 1.30 | 1.30 | 100 | 1.30 | 100 |
| XVII | 1.32 | 1.29 | 98 | 1.19 | 90 |
| XVIII | 1.28 | 1.28 | 100 | 1.23 | 96 |
| XIX | 1.35 | 1.33 | 99 | 1.31 | 97 |
| XX | 1.28 | 1.28 | 100 | 1.24 | 97 |
| XXI | 1.27 | 1.27 | 100 | 1.27 | 100 |
| XXII | 1.30 | 1.30 | 100 | 1.30 | 100 |
| Comparative example NKK 1304 | 1.25 | 1.27 | 100 | 1.20 | 96 |
| Comparative example PF 201 | 1.21 | 1.18 | 98 | 0.79 | 65 |

*Percentage of remaining image density in accordance with Eq. 1

It can be deduced from the above examples that the heat-sensitive recording material of the present invention shows the following advantageous properties especially:

(1) The recorded image of the heat-sensitive recording materials based on the colour developers according to the invention has print densities (optical densities) which are better than/comparable to those of the comparative examples with known colour developers (Table 3).
(2) The temperature from which a visually perceptible greying of the recording materials according to the invention occurs (static starting point) is comparable to or higher than that of the comparative examples with known colour developers (Table 3).
(3) The heat-sensitive recording materials subjected to the ageing test reveal a high image stability, better than or comparable to that of the comparative examples with known colour developers (Table 3).
(4) The printed image is hardly faded or only slightly faded following the effect of hydrophobic agents (adhesives, plasticisers). The image resistance is better in comparison to heat-sensitive recording materials with known non-phenolic colour developers and largely satisfies the requirements of marketable heat-sensitive recording materials (Table 4).
(5) Printing of the heat-sensitive recording materials stored for several weeks under extreme conditions results in image densities that are practically identical to those of unstored (fresh) heat-sensitive recording materials (Table 5).
(6) A heat-sensitive recording material that is considered to be high-quality in all key respects of its application can be obtained with the colour developers according to the invention. No recording material based on known colour developers has a comparably good/balanced performance profile over all tested properties.

The invention claimed is:
1. A compound of formula (I),

$$Ar^1-NH-CO-NH-C_6H_4-SO_2-O-C_6H_4-NH-CO-NH-Ar^2 \quad (I),$$

wherein $Ar^1$ and $Ar^2$ independently of one another are an unsubstituted or substituted phenyl group, naphthyl group and/or heteroaryl group.

2. The compound according to claim 1, wherein $Ar^1$ is a phenyl group.

3. The compound according to claim 1, wherein $Ar^2$ is a phenyl group.

4. The compound according to claim 1, wherein $Ar^1$ is substituted with at least one $C_1$-$C_5$ alkyl group, an alkenyl group, an alkynyl group, a benzyl group, a formyl group, a halogen group, an $NO_2$ group, a CN group, an R—CO group, an RO group, an $RO_2C$ group, an R—OCO group, an R—$SO_2$O group, an R—O—$SO_2$ group, an R—$SO_2$—NH group, an R—NH—$SO_2$ group, an R—NH—CO group or an R—CO—NH group, wherein R is a $C_1$-$C_5$ alkyl group, an alkenyl group, an alkynyl group, a phenyl group, a tolyl group, or a benzyl group.

5. The compound according to claim 1, wherein $Ar^1$ is substituted once.

6. The compound according to claim 1, wherein $Ar^2$ is substituted with at least one $C_1$-$C_5$ alkyl group, an alkenyl group, an alkynyl group, a benzyl group, a formyl group, a halogen group, an $NO_2$ group, a CN group, an R—CO group, an RO group, an $RO_2C$ group, an R—OCO group, an R—$SO_2$O group, an R—O—$SO_2$ group, an R—$SO_2$—NH group, an R—NH—$SO_2$ group, an R—NH—CO group or an R—CO—NH group, wherein R is a $C_1$-$C_5$ alkyl group, an alkenyl group, an alkynyl group, a phenyl group, a tolyl group, or a benzyl group.

7. The compound according to claim 1, wherein $Ar^2$ is substituted once.

8. The compound according to claim 1, wherein $Ar^1$ is a phenyl group, and wherein $Ar^2$ is a phenyl group.

9. The compound according to claim 1, wherein the $Ar^1$—NH—CO—NH group and the $Ar^2$—NH—CO—NH group are arranged respectively in the 2 and 3', in the 2 and 4', in the 3 and 2', in the 3 and 3', in the 3 and 4', in the 4 and 2', in the 4 and 3' or in the 4 and 4' position relative to the —$C_6H_4$—$SO_2$—O—$C_6H_4$ group.

10. The compound according to claim 1, wherein Ar1 is substituted once.

11. The compound according to claim 1, wherein Ar2 is substituted once.

12. The compound according to claim 9, wherein the $Ar^1$—NH—CO—NH group and the $Ar^2$—NH—CO—NH group are arranged respectively in the 3 and 2' or 4 and 3' position relative to the —$C_6H_4$—$SO_2$—O—$C_6H_4$ group.

13. A heat-sensitive recording material comprising a carrier substrate and a heat-sensitive colour-forming layer, which contains at least one colour former and at least one phenol-free colour developer, wherein the at least one colour developer is the compound of formula (I) according to claim 1.

14. The heat-sensitive recording material according to claim 10, wherein the colour developer is present in an amount of from about 3 to about 35% by weight in relation to the total solids content of the heat-sensitive layer.

15. The heat-sensitive recording material according to claim 13, wherein the at least one colour former is a triphenylmethane dye, a fluoran dye, an azaphthalide dye and/or a fluorine dye.

16. The heat-sensitive recording material according to at least one of claim 13, wherein one or more non-phenolic colour developers are present in addition to the phenol-free colour developer.

17. The heat-sensitive recording material according to claim 13, wherein the colour developer is present in an amount of from about 10 to about 25% by weight in relation to the total solids content of the heat-sensitive layer.

18. A method for producing a heat-sensitive recording material according to claim 13, wherein an aqueous suspension containing—the at least one colour former and the at least one phenol-free colour developer of the heat-sensitive colour-forming layer is applied to a carrier substrate and dried, wherein the aqueous application suspension has a solids content of from about 20 to about 75% by weight and is applied and dried by a curtain coating process at an operating speed of at least about 400 m/min.

19. A heat-sensitive recording material obtainable obtained by the method according to claim 18.

20. A method for producing a heat-sensitive recording material according to claim 13, wherein an aqueous suspension containing the at least one colour former and the at least one phenol-free colour developer of the heat-sensitive colour-forming layer is applied to a carrier substrate and dried, wherein the aqueous application suspension has a solids content of from about 30 to about 50% by weight and is applied and dried by a curtain coating process at an operating speed of at least about 1000 m/min.

* * * * *